United States Patent
Sakakibara et al.

(12)

(10) Patent No.: US 6,770,747 B1
(45) Date of Patent: Aug. 3, 2004

(54) GENES ENCODING PROTEIN HAVING ACTIVITY OF TRANSFERRING SUGAR ONTO AURONE

(75) Inventors: Keiko Sakakibara, Muko (JP); Yuko Fukui, Osaka (JP); Yoshikazu Tanaka, Otsu (JP); Takaaki Kusumi, Suita (JP); Takafumi Yoshikawa, Chigasaki (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/673,300

(22) PCT Filed: Feb. 16, 2000

(86) PCT No.: PCT/JP00/00876

§ 371 (c)(1),
(2), (4) Date: Oct. 16, 2000

(87) PCT Pub. No.: WO00/49155

PCT Pub. Date: Aug. 24, 2000

(30) Foreign Application Priority Data

Feb. 16, 1999 (JP) ............................................ 11-036801

(51) Int. Cl.⁷ ............................................... C07H 21/04
(52) U.S. Cl. .................... 536/23.1; 435/320.1; 435/410; 435/252.3
(58) Field of Search .............................. 536/23.1, 24.31; 435/468, 440, 193, 410, 320.1; 800/278, 295, 323

(56) References Cited

PUBLICATIONS

Halbwirth, H. et al., "Enzymatic glucosylation of 4–deoxyaurones and 6'–deoxychalcones with enzyme extracts of Coreopsis grandiflora, Nutt. I.", Plant Sci. (Jan. 1997) vol. 122, No. 2, p. 125–131.

Horvath, D.M. et al., "Identification of an immediate–early salicylic acid–inducible tobacco gene and characterization of induction by other compounds.", Plant Mol. Biol. (Aug. 1996), vol. 31, No. 5, p. 1061–1072.

Database GenBank Accession No. AB031274, Aug. 18, 1999, Hirotani, M. et al., "Scutellaria baicalensis ufgt mRNA for UDP–glucose:flavonoid 7–0–glucosyltransferase, complete cds.".

*Primary Examiner*—Jeffrey Fredman
*Assistant Examiner*—Juliet C. Switzer
(74) *Attorney, Agent, or Firm*—Burns, Doane, Swecker & Mathis, L.L.P.

(57) ABSTRACT

There is provided a gene encoding a protein derived from, for example, snapdragons and petunias, said protein having an amino acid sequence as set forth in SEQ ID NO: 2, 8, and 10, and having an activity of transferring a glycosyl group to aurones, and a method of producing said protein using said gene. By introducing this gene into plants that do not have said gene, a yellow pigment aurone can be stabilized and plants having yellow flowers can be obtained.

6 Claims, 2 Drawing Sheets

Fig. 1

GENES ENCODING PROTEIN HAVING ACTIVITY OF TRANSFERRING SUGAR ONTO AURONE

TECHNICAL FIELD

The present invention relates to a gene encoding a protein having a glycosyl transferase activity to aurones, said protein, and the uses thereof.

BACKGROUND ART

The color of flowers are mainly based on three pigments: flavonoids, carotenoids, and betalains. Yellow colors are mostly derived from carotenoids and betalains, but in some plants they are derived from flavonoids. Among the flavonoid pigments, major pigments that are thought to be associated with the development of yellow flowers are divided into three groups: chalcones, aurones, and yellow flavonols (Saito, Biohorti 1, pp. 49–57, 1990)

Aurones are substances in which two phenyl groups are joined together through three carbon atoms of dihydrofuran. As aurones, there are known 4,6,4'-trihydroxy aurone, aureusidin, sulfuretin, bracteatin, and the like. For example, aureusidin and bracteatin are contained in snapdragons, aureusidin is contained in limoniums, aureusidin is contained in morning glories, sulfuretin is contained in dahlias, bracteatin is contained in *Helichrysum bracteatum*, and sulfuretin is contained in *Helianthus tuberosus*.

Flavonoids have generally been modified by acylation, glycosilation, methylation and the like, and carotenoids and betalains have also been glycosilated in many cases. Among various modifications, glycosilation plays an important role in the color of flowers such as (1) contribution to enhancing the stability and solubility of pigments, (2) the presence as a step preceding acylation that greatly affects the hue of colors, and (3) copigmentation effects by the glycosilated flavonoids, and the like.

It has been reported that, in snapdragon, a yellow pigment aurones (aureusidin, bracteatin), a kind of flavonoid, is present in a glycosilated at its position 6 corresponding to position 7 of flavonoids, and since aurones are present as glycosides in other aurone-containing plants as well, it has been considered that glycosilation is essential for the stability of aurones.

There are many reports on the genes for glycosyl transferases derived from plants that transfer a glycosyl group to flavonoids and on the activities of those enzymes.

By way of example, genes encoding UDP-glucose: flavonoid 3-glucosyl transferases (3GT) that transfer a glycosyl group to the position 3 of flavonoids have been obtained from many plants including corn, barley, and snapdragon, and has been analyzed in detail (The Flavonoids: Advanced in Research Since 1986. Published by Chapman & Hall, 1993).

Also, genes encoding UDP-glucose: flavonoid 5-glucosyl transferases (5GT) that transfer a glycosyl group to the position 5 of flavonoids have been cloned from perillas, torenias, and verbenas (International Patent Publication No. WO 99/05287).

However, as to the gene encoding UDP-glucose: flavonoid 7-glucosyl transferase (7GT) that transfers a glycosyl group to the position 7 of flavonoids, there is only one report on the purification of flavanone-specific 7-glucosyl transferase in grapefruits (Archives of Biochemistry and Biophysics 282, 1: 50–57, 1990).

With regard to enzymes that transfer a glycosyl group to the position 6 of aurones, there is a report on the measurement of a reaction that transfers a glycosyl group to the position 6 of sulfuretin, a kind of aurone (Plant Science 122: 125–131, 1997), but this only studied the enzymatic property using a partially purified product, and has not been purified in a pure form.

On the other hand, there is a report on the isolation of a glycosyl transferase, pS.b UFGT1, that has an activity of transferring glucose to the position 7 of baicaleins, a kind of flavone, from the hairy roots of a Labuatae, *Scutellaria baicalensis* (1997, presented at the Fifteenth annual meeting of Japanese Society of Plant Cell and Molecular Biology). The gene product is also reported to be capable of transferring a glycosyl group to the position 7 of anthocyanidins and flavonols, but not reported on aurones (presented at the Fifteenth annual meeting of Japanese Society of Plant Cell and Molecular Biology).

As genes having a high homology to pS.b UFGT1, tabacco-derived IS10a and IS5a have been reported (Plant Molecular Biology, 31: 1061–1072, 1996), but its activity of transferring a glycosyl group to position 7 (7GT activity) has not been studied.

Reports to date teach that the glycosyl transferases that use flavonoids as substrates have a great variation in substrate specificity even among flavonoids. For example, when the gene of flavonoid-3-glycosyl transferase derived from gentians were cloned, expressed in *E coli*, and the activity was determined, it was found to exhibit a 61% activity to cyanidins, a 38% activity to pelargonidins, and a good activity to anthocyanins relative to a 100% glycosyl transferase activity to delphinidins. On the other hand, it only shows an activity of 7.0%, 6.5%, and 4.4% to kaempferol, quercetin, and myricetin, respectively. Furthermore, it does not transfer a glycosyl group to dihydroflavonols (Tanaka et al., Plant Cell Physiol. 37: 711, 1996).

Also, when the gene of flavonoid-3-glycosyl transferase derived from grapes was cloned and the activity was determined in *E. coli*, its Km was 30 $\mu$M and Vmax was 905 nkatals/mg to cyanidins, whereas to quercetins the Km was 15 $\mu$M and Vmax was 18.9 nkatals/mg, exhibiting a great difference in reaction rates (Ford et al., J. Biol. Chem. 273: 9224, 1998).

These reports indicate that glycosyl transferases can distinguish the kinds of flavonoids and that the glycosyl transferase activity to a flavonoid does not readily permit the estimation of the glycosyl transferase activity to another flavonoids.

DISCLOSURE OF THE INVENTION

As hereinabove described, glycosyl transferases using flavonoids as substrates have a great variation in substrate specificity and the estimation of a glycosyl transferase activity to a specific flavonoid cannot be easily made based on known glycosyl transferases.

Thus, the present inventors have attempted to obtain a gene encoding a protein having a glycosyl transferase activity to aurones among the flavonoid pigments, and thereby have completed the present invention.

The present inventors have demonstrated that a gene product of the pS.b UFGT1 gene derived from *Scutellaria baicalensis* has an activity of transferring a glycosyl group to aurones, and, using this gene as a probe, have obtained a gene encoding a protein having an activity of transferring a glycosyl group to aurones from snapdragons (*Antirrhinum majus*).

Also, using said gene obtained from snapdragons (*Antirrhinum majus*) as a probe, the present inventors have further obtained two genes encoding a protein having an activity of transferring a glycosyl group to aurones from a petunia (*Petunia hybrida*).

Thus, the present invention provides a gene encoding a protein having an activity of transferring a glycosyl group to aurones. Furthermore, the present invention provides a gene encoding a protein having the amino acid sequence as set forth in SEQ ID NO: 2, 8, or 10 and having an activity of transferring a glycosyl group to aurones.

The present invention further provides a gene encoding a protein that has an amino acid sequence modified by the addition, deletion and/or substitution with other amino acids of one or more amino acids in the amino acid sequence as set forth in SEQ ID NO: 2, 8, or 10, and that has an activity of transferring a glycosyl group to aurones.

The present invention further provides a gene encoding a protein that hybridizes to a nucleic acid having a nucleotide sequence encoding the amino acid sequence as set forth in SEQ ID NO: 2, 8, or 10 or a portion thereof under a stringent condition, and that has an activity of transferring a glycosyl group to aurones.

The present invention also provides a vector comprising said gene.

The present invention further provides a host transformed with said vector. The host may be a microorganism, plant cells, animal cells, or plants.

The present invention also provides a method of producing a protein having an activity of transferring a glycosyl group to aurones, by culturing, cultivating or breeding said host.

The present invention also provides a method of stabilizing aurones in the plant, said method comprising introducing said gene into the plant having aurones, allowing said gene to be expressed, and transferring a glycosyl group to aurones in the plants with a protein thus produced.

In cases where a new flower color is to be created by introducing and expressing the gene of an aurone synthase in plants that have no aurones, aurones can be stably expressed therein by expressing the gene obtained by the present invention.

EMBODIMENTS FOR CARRYING OUT THE INVENTION

First, a cDNA library is prepared from the petals of a yellow snapdragon. The cDNA library thus obtained is screened using pS.b UFGT1, a flavonoid-7-glycosyl transferase gene derived from *Scutellaria baicalensis*, and then a clone is obtained. The plasmid obtained from the clone is isolated and its nucleotide sequence is determined.

It is known that enzymatically active proteins have regions essential for the enzymatic activity and regions non-essential for the activity, and that the enzymatic activity is retained even when the non-essential regions are modified by the addition, deletion and/or substitution with other amino acids of one or more amino acids. Thus, the present invention encompasses not only a protein having an amino acid sequence as set forth in SEQ ID NO: 2, 8, or 10, but also a protein having an amino acid sequence modified by the addition, deletion and/or substitution with other amino acids of one or more amino acids in the amino acid sequence as set forth in SEQ ID NO: 2, 8, or 10, and that having an activity of transferring a glycosyl group to aurones, and a gene encoding said protein.

The number of amino acids to be modified is, for example, 50 or less, and preferably 30 or less, for example 20 or less or 10 or less.

The gene encoding the protein having an amino acid sequence as set forth in SEQ ID NO: 2, B, or 10 can be obtained as cDNA or genomic DNA from snapdragons or petunias. The method of cloning cDNA is specifically described in Examples 2, 3 and 6. In order to obtain genomic DNA, a genomic library is constructed based on the standard method from snapdragons or petunias and then screened using said cDNA or a fragment thereof according to the standard method.

A gene encoding a protein having an amino acid sequence modified in the amino acid sequence as set forth in SEQ ID NO: 2, 8, or 10 can be constructed by modifying a nucleotide sequence of a DNA, for example cDNA, encoding a protein having an amino acid sequence as set forth in SEQ ID NO: 2, 8, or 10, by a standard method for manipulating genes such as site-directed mutagenesis and the PCR method.

Once a gene encoding a protein having the enzymatic activity has been cloned, the nucleic acid that hybridizes to said gene or a portion thereof encodes, in most cases, an amino acid sequence that exhibits the enzymatic activity and that is similar to the original protein. Thus the present invention provides a gene that hybridizes to a nucleic acid having a nucleotide sequence encoding an amino acid sequence as set forth in SEQ ID NO: 2, 8, or 10 or a portion thereof under a stringent condition, and that encodes a protein having an activity of transferring a glycosyl group to aurones.

In the above hybridization condition, the washing condition is preferably 5×SSC, 0.1% SDS and 50° C., more preferably 2×SSC, 0.1% SDS and 50° C., and more preferably 0.1×SSC, 0.1% SDS and 50° C.

In the above hybridization, when a nucleic acid having a portion of the nucleotide sequence encoding an amino acid sequence as set forth in SEQ ID NO: 2, 8, or 10 is used, the length of the nucleic acid is preferably at least 17 base pairs long, and more preferably at least 100 base pairs long. As target nucleic acids to be hybridized, there can be used nucleic acids prepared from *Scutellaria baicalensis*, snapdragons, petunias, limoniums, mornig glories, dahlias, *Helichrysum bracteatum, Helianthus tuberosus*, and the like, and preferably genomic DNA libraries or cDNA libraries are used.

The present invention also provides a method of producing the above protein having an activity of transferring a glycosyl group to aurones. The method comprises introducing a vector comprising DNA encoding said protein into a host, culturing or growing said host, and recovering said protein as desired. The host may be host cells or plants, etc.

As the host cells, there can be used prokaryotic cells, particularly bacteria cells such as cells of *Escherichia coli*, a bacterium belonging to the genus Bacillus such as *Bacillus subtilis* and *Bacillus brevis*, lower eukaryotes such as fungi, for example yeast such as a yeast belonging to the genus Saccharomyces, for example *Saccharomyces cerevisiae*, or filamentous fungi such as the genus Aspergillus, for example *Aspergillus oryzae* and *Aspergillus niger*, and the like.

Furthermore, as higher eukaryotic hosts, there can be mentioned insect cells such as cells of silkworm, animal cells such as CHO cells, cultured human cells such as HeLa cells, and the like.

The gene of the present invention may also be expressed in an organism of, for example, a plant and so on.

Vectors comprising the DNA of the present invention, expression vectors in particular, may contain expression regulatory regions, and the expression regulatory regions depend on the host cell. For example, as promoters for bacterial expression vectors, there can be mentioned commonly used promoters such as the trc promoter, the tac promoter, the lac promoter, the T7 promoter and the like; as promoters for yeast expression vectors, there can be used the promoters of the genes of the glycolytic pathway such as glyceraldehyde-3-phosphate dehydrogenase promoter, galactokinase promoter, and the like; and as promoters for animal cell expression vectors, viral promoters can be used.

In order to recover proteins having an activity of transferring a glycosyl group to aurones, methods commonly used for isolation and purification of protein can be used such as liquid chromatography, and affinity chromatography.

With the current state in the art, it is possible to further ligate the cDNA under the control of a constitutive or inducible promoter, and introduced into a plant such as petunia, rose, carnation, chrysanthemum, torenia, verbena, gerbera, tobacco, strawberry, lisianthus, gentian, gladiolus, and tulip in a system utilizing Agrobacterium, particle guns, or electroporation, and to express the gene encoding the protein having an activity of transferring a glycosyl group to aurones in flower petals.

It is expected that in the flower petals in which a protein having an activity of transferring a glycosyl group to aurones was expressed, the aurones are glycosilated, and thereby are stabilized. The plants thus obtained can provide flowers having a hue of color that cannot be found in the conventional varieties.

In plants having no aurones, an aurone synthase gene are introduced, expressed, and at the same time a gene of the present invention encoding the protein having an activity of transferring a glycosyl group to aurones can be introduced and expressed, so that aurones can be stably expressed and new plants having a yellow hue can be provided. As the above plants having no aurones, there can be mentioned petunias, torenias, and tobaccoes.

EXAMPLES

The present invention will now be explained in further details with reference to the following Examples.

Example 1

Measurement of the Activity of Transferring a Glycosyl Group to Aurones of a Product of the pS.b UFGT1 Gene Derived from *Scutellaria baicalensis*

The activity of the pS.b UFGT1 gene derived from *Scutellaria baicalensis* of transferring a glycosyl group to aurones was determined using an expression vector pESBGT-1 in *E. coli* prepared by the following method.

First, the pS.b UFGT1 gene was subjected to a PCR reaction using two primers to introduce NdeI and BamHI sites.

5'-ATA ACT ACA TAT GGG ACA ACT CCAC-3' (SEQ ID NO: 3)

5'-CAG AAC AGG ATC CAC ACG TAA TTT A-3' (SEQ ID NO: 4)

The PCR reaction mixture was prepared in a total volume of 50 μl comprising 300 ng of pSBGT-1, 1×Native Pfu DNA polymerase reaction buffer (Stratagene), 0.2 μM dNTPs, 4 pg/μl each of the primers, and 2.5 U of Native Pfu DNA polymerase. The reaction was carried out, after 3 minutes at 95° C., for 30 cycles with one cycle comprising 95° C. for 1 minute, 50° C. for 2 minutes, and 72° C. for 2 minutes, and finally was treated at 72° C. for 7 minutes.

Figure 1:
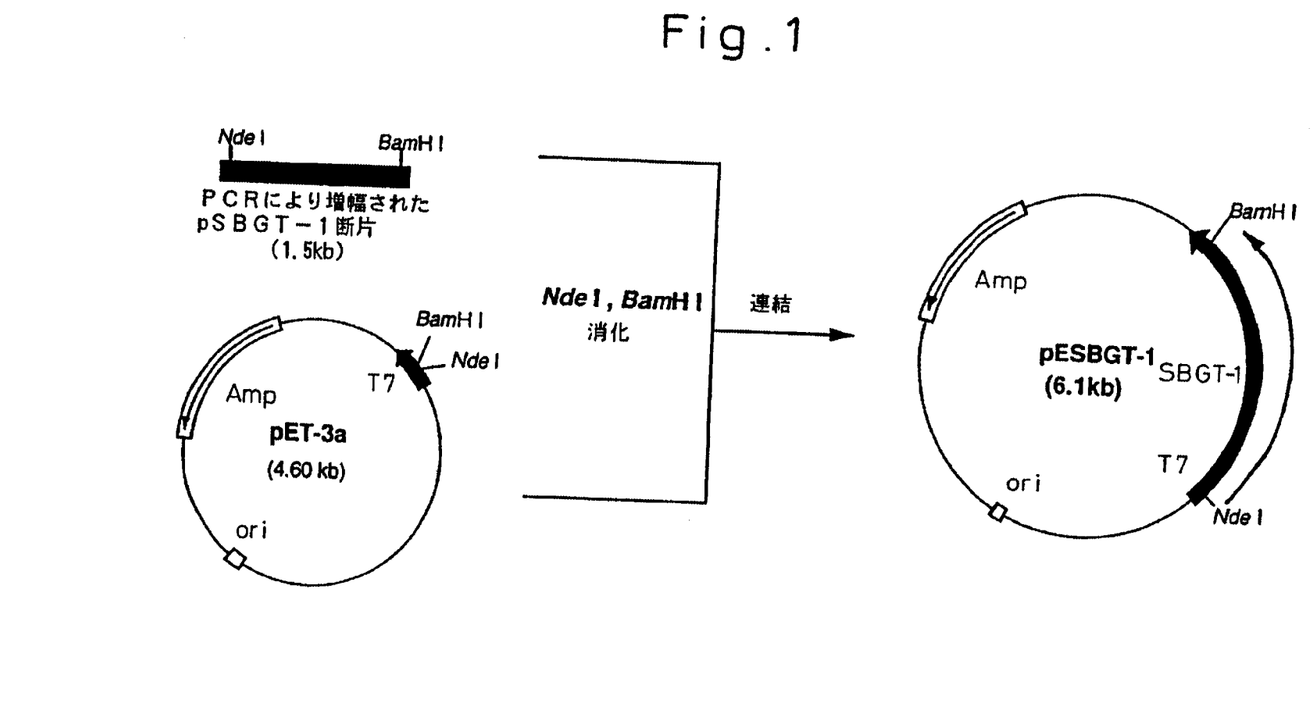
FIG. 1 shows a process of constructing the plasmid pESBGT-1.

The PCR product was digested with NdeI and BamHI, and then was ligated to the NdeI- and BamHI-digested pET-3a vector (Stratagene) to construct pESBGT-1 (FIG. 1). Using each of pESBGT-1 and pET-3a vector, it was transformed into *Epicurian Coli* BL21 (DE3) (Stratagene). The transformants were incubated overnight at 37° C. in 3 ml of a LB medium containing 50 μg/ml of ampicillin. The preculture (500 μl) was added to 50 ml of a LB medium containing 50 μg/ml of ampicillin, and cultured until A600 reached 0.6–1.0. Then isopropyl-β-D-thiogalactopyranoside (IPTG) was added thereto to a final concentration of 0.5 mM, which was cultured at 28° C. for 4 hours and centrifuged (5000 rpm, 10 minutes, 4° C.) to collect the cells.

The pellets were suspended in 5 ml of the buffer (10 mM sodium phosphate, pH 6.5, 1 mM β-mercaptoethanol (2-ME)). After the *E. coli* cells were disrupted by a sonicator, it was centrifuged (15,000 rpm, 5 minutes, 40° C.), and the supernatant obtained was used as a crude enzyme solution for the next enzyme reaction.

In addition to aureusidin, the enzymatic activity was determined using naringenin or luteolin as the substrate.

For aureusidin, the enzymatic activity was determined as follows:

To 50 μl of the crude enzyme solution were added 0.1 M Tris-HCl, pH 8.0, and 150 μl of 0.05% 2-ME, and then incubated at 30° C. for 10 minutes. Then 5 μl of 4.66 mM aureusidin and 50 μl of 5 mM UDP-glucose were added thereto, and was allowed to react at 30° C. for 1 hour. After the reaction was stopped by adding 200 μl of 90% acetonitrile containing 5% trifluoroacetic acid (TFA), it was centrifuged at 15,000 rpm and 4° C. for 3 minutes. The supernatant thus obtained was filtered (pore size 0.45 μm, 4 mm Millex-LH, Millipore) to remove insoluble substances. The filtrate was analyzed by high performance liquid chromatography.

The analytical condition was as follows: The column used was Asahipak-ODP-50 (4.6 mm φ×250 mm, Showa Denko). The mobile phase comprised water containing 0.1% TFA as solution A and 90% CH$_3$CN containing 0.1% TFA as solution B. After a linear gradient from 20% solution B to 100% solution B for 20 minutes, 100% solution B was retained for 5 minutes. The flow rate was 0.6 ml/min. Detection used A380 nm, and an absorption spectrum at 250–400 nm using Shimadzu PDA detector SPD-M6A.

For a reaction of the crude extract of *E. coli* cells in which pESBGT-1 was expressed, new substances were detected that eluted at 9.7, 12.0, and 13.1 minutes in addition to the substrate aureusidin (retention time 18.1 minutes). Since they were not detected in a reaction of the crude extract similarly prepared from *E. coli* cells in which the pET-3a vector was expressed, they were considered to be products resulting from the protein derived from pESBGT-1. The substance that eluted at 12.0 minutes among the products had the same retention time and the same absorption spectrum as that of aureusidin 6-glycoside. Other products also are considered to be aureusidin glycosides based on the absorption spectra.

For naringenin and luteolin, the enzymatic activity was determined as follows.

To 20 µl of the crude enzyme solution were added 25 µl of 0.1 M citric acid-phosphate buffer, pH 6.5, 5 µl each of 5 µM substrate, and 25 µl of 5 mM UDP-glucose in a total volume of 250 µl, and then incubated at 30° C. for 30 minutes. After the reaction was stopped by adding 200 µl of 90% acetonitrile containing 5% TFA, it was centrifuged at 15,000 rpm and 40° C. for 3 minutes. The supernatant thus obtained was filtered (pore size 0.45 µm, 4 mm Millex-LH, Millipore) to remove insoluble substances. The filtrate was analyzed by high performance liquid chromatography.

The analytical condition for naringenin was follows: The column used was YMC J's sphere ODS-M80 (4.6 mm φ×150 mm, YMC). The mobile phase comprised water containing 0.1% TFA as solution A and 90% $CH_3CN$ containing 0.1% TFA as solution B. After a linear gradient from 20% solution B to 80% solution B for 10 minutes, 80% solution B was retained for 5 minutes. The flow rate was 0.6 ml/min. Detection used A290 nm, and an absorption spectrum at 250–400 nm using Shimadzu PDA detector SPD-M6A.

The analytical condition for luteolin was as follows: The column used was YMC J's sphere ODS-MB80 (4.6 mm φ×150 mm, YMC). The mobile phase comprised water containing 0.1% TFA as solution A and 90% $CH_3CN$ containing 0.1% TFA as solution B. After a linear gradient from 20% solution B to 80% solution B for 10 minutes, 80% solution B was retained for 5 minutes. The flow rate was 0.6 ml/min. Detection used A330 nm, and an absorption spectrum at 250–400 nm using Shimadzu PDA detector SPD-M6A.

When naringenin was used as the substrate, a new substance was detected that eluted at 6.9 minutes in addition to the naringenin (retention time 9.7 minutes). The substance was not detected in a reaction of the crude extract similarly prepared from *E. coli* in which the pET-3a vector was expressed. It had the same retention time as naringenin 7-glycoside but a different absorption spectrum, suggesting that a plurality of naringenin glycosides are present each at a trace amount.

When luteolin was used as the substrate, new substances were detected that eluted at 6.4, 7.7, and 8.0 minutes that were not be detected in a reaction of the crude extract similarly prepared from *E. coli* in which the pET-3a vector was expressed. The substance that eluted at 6.4 minutes among them had the same retention time as luteolin 7-glycoside.

The above result indicated that the pS.b UFGT1 gene derived from *Scutellaria baicalensis* is an enzyme that can glycosilate aureusidin. It was also demonstrated that it can glycosilate luteolin but had very little effect on naringenin.

It has already been shown that baicalein can be glycosilated at the position 7. After the reaction is complete for baicalein, almost 100% is detected as a 7 glycoside, but no reaction occurred to naringenin indicating that the expression product of the *Scutellaria baicalensis*-derived pS.b UFGT1 gene has a high substrate specificity.

Example 2

Construction of cDNA Library of Snapdragon Petals

A cDNA library of the petals was prepared as follows: From 5 g of fresh petals of a yellow snapdragon (yellow butterfly), RNA was obtained using a method of employing guanidine thiocyanate and cesium chloride as described in detail in Method in Molecular Biology, Vol. 2, (Humana Press Inc., 1984) by R. McGookin et al., and polyA+RNA was purified therefrom using Oligotex dT30 (Nippon Roche). From the polyA+RNA, cDNA library was constructed using the cDNA synthesis kit, Uni-XR vector kit (Stratagene). The library obtained comprised $1.6×10^5$ plaque forming units (pfu).

Example 3

Collection of the Full-length Aurone Glycosyl Transferase

The snapdragon cDNA library obtained in Example 2 was screened using the full-length ps.b UFGT1, a hairy root-derived flavonoid-7-glycosyl transferase. The if library was screened using a non-radio system DNA detection kit (Boehringer). Hybridization was carried out overnight at 37° C. Washing filter was carried out at 5×SSC, 0.1% SDS and 50° C. for 30 minutes. About 200,000 plaques were screened to finally obtain 2 clones. The method was based on Molecular Cloning (Sambrook et al., Cold Spring Harbour Laboratory Press, 1989).

Since the two clones encoded the sequences having the completely same length, one was designated as pAmGT1 and nucleotide sequence was determined.

The nucleotide sequence was determined by synthesizing an oligonucleotide primer and using DNA Sequencer model 310 (Applied Biosystems). The nucleotide sequence and the deduced amino acid sequence are shown in SEQ ID NO:. 1 in the sequence listing. pAmGT1 contained a 1751 bp gene AmGT1 encoding a protein of a molecular weight 53.9 kDa comprising 481 amino acids.

Example 4

Expression of the AmGT1 cDNA in *E. coli*

The expression of the AmGT1 cDNA was carried out using the pET System (Stratagene).

First, in order to introduce NdeI and BamHI sites, the following 2 primers pETAmGT5' and pETAmGT3' were used in a PCR reaction.

pETAmGT5': 5'-ATA ACT ACA TAT GGG AAA ACT TCA C-3' (SEQ ID NO: 5)

pETAmGT3': 5'-GAA CAG GAT CCA CAC ACT AGA AGT CA-3' (SEQ ID NO: 6)

The PCR reaction mixture was prepared in a total volume of 100 µl comprising 100 ng of pAmGT1, the 1×the cloned Pfu DNA polymerase reaction buffer (Stratagene), 0.2 mM dNTPs, 0.5 pmol/µl each of the primers, and 5.0 U of the cloned Pfu DNA polymerase. The reaction was carried out, after 45 seconds at 95° C., for 25 cycles with one cycle comprising 95° C. for 45 seconds, 50° C. for 45 seconds, and 72° C. for 2 minutes, and was finally treated at 72° C. for 10 minutes. The PCR product obtained was subcloned into the pCR2.1 TOPO vector (INVITROGEN).

Figure 2:
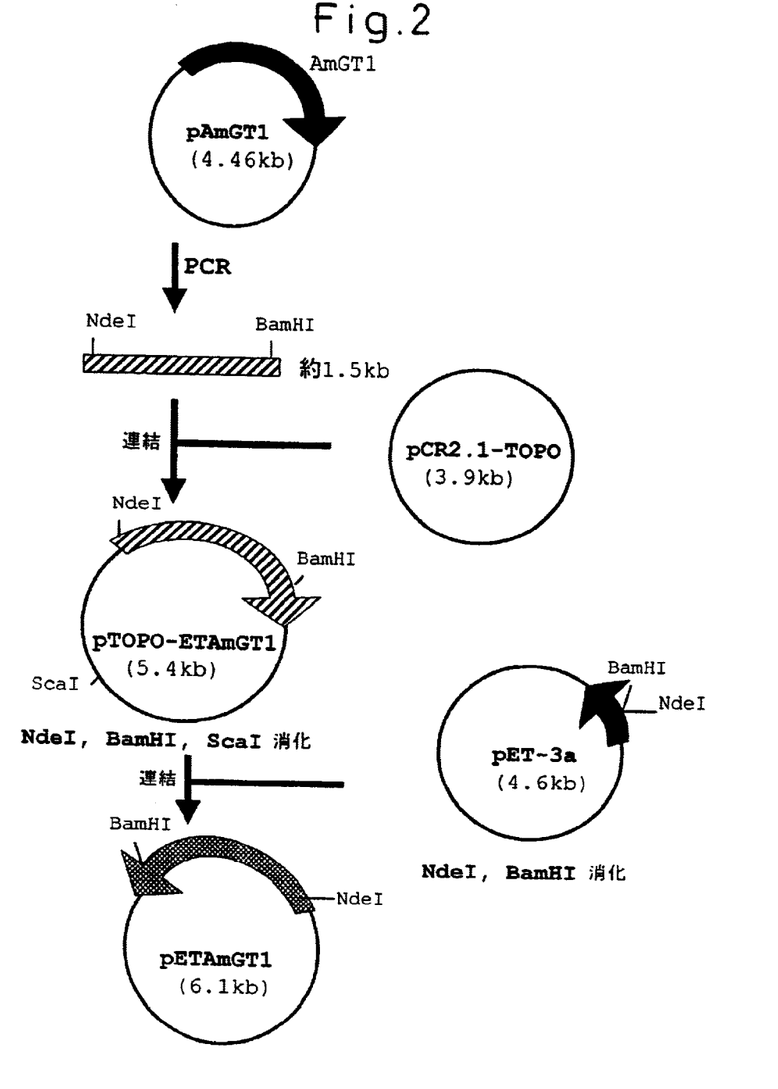
FIG. 2 shows a process of constructing the plasmid pETAmGT1.

Some of the clones of the plasmid pTOPO-ETAmGT1 thus obtained were reacted using M13 Reverse Primer and M13(-20) primer (TOYOBO) using ABI PRISM™ Big-Dye™ Terminator Cycle Sequencing Ready Reaction Kit (Applied Biosystems), and the nucleotide sequences on both ends were confirmed using DNA Sequencer model 310 (Applied Biosystems). An about 2.7 Kb fragment obtained by digesting pTOPO-ETAmGT1 with NdeI, BamHI and ScaI was ligated to the NdeI and BamHI sites of the pET-3a vector (Stratagene) to obtain plasmid pETAmGT1 (FIG. 2). Using pETAmGT1, it was transformed into Epicurian Coli BL21 (DE3) (Stratagene).

Example 5

Measurement of the Glycosyl Transferase Activity of the AmGT1 cDNA Recombinant Protein The transformant obtained in Example 4 was cultured, extracted and the enzymatic activity was measured as in Example 1.

When aureusidin was used as the substrate, new substances were detected that eluted at 10.98, 11.27, and 11.85 minutes in addition to aureusidin (retention time 16.6 minutes). Since the substances were not detected in a reaction of the crude extract similarly prepared from *E. coli* in which the pET-3a vector was expressed, they were believed to be products that resulted from pESBGT-1-derived protein.

Among the products, the substance that eluted at 10.98 minutes had the same retention time as aureusidin 6-glycoside, and the one that eluted at 11.85 minutes had the same retention time as aureusidin 4-glycoside.

The above results indicated that AmGT1 can transfer a glycosyl group to the positions 6 and 4 of aureusidin. The substance that eluted at 11.27 minutes is also believed to be aureusidin glycoside based on the absorption spectra.

Example 6

Preparation of the Gene of Aurone Glycosyl Transferase Derived from Petunias A cDNA library obtained from petals of a petunia variety "old Glory Blue" (Nature 366: 276–279, 1993) was screened with the full-length AmGT1 gene obtained in Example 3. The library was screened using a non-radio system DNA detection kit (Boehringer). Hybridization was carried out overnight at 37° C. Washing filter was carried out at 5×SSC, 0.1% SDS, and 50° C. for 30 minutes. About 200,000 plaques were screened to finally obtain 2 clones. The method was based on Molecular Cloning (Sambrook et al., Cold Spring Harbour Laboratory Press, 1989).

The two clones were designated as pPh7GTa and pPh7GTb, respectively, and the nucleotide sequences were determined. The nucleotide sequence was determined by synthesizing an oligonucleotide primer and using DNA Sequencer model 310 (Applied Biosystems). The nucleotide sequence at the insertion site of pPh7GTa and the deduced amino acid sequence are shown in SEQ ID NO: 7 and 8, respectively, and the nucleotide sequence at the insertion site of pPh7GTb and the deduced amino acid equence are shown in SEQ ID NO: 9 and 10, respectively.

Example 7

Structural Analysis of the Gene of Aurone Glycosyl Transferase pPh7GTa contained a 1750 bp gene, Ph7GTa, encoding a protein comprising 488 amino acids, and pPh7GTb contained a 1669 bp gene, Ph7GTb, encoding a protein comprising 476 amino acids. Using the deduced amino acid sequences obtained, they were compared with the AmGTI gene derived from Snapdragon obtained Example 3 and the pS.b UFGT1 gene derived from *Scutellaria baicalensis*. Accordingly, it was found that Ph7GTa had a 50% and 51% homology with AmGT1 and pS.b UFGT1, respectively. When compared with IS5a and IS10a derived from tobaccoes that are already reported to be genes having a high homology with pS.b UPGT1, they have exhibited homologies of 59% and 60%, respectively. Similarly, Ph7GTb had homologies of 59% and 56% with AmGT1 and pS.b UFGT1, respectively, and homologies of 88% and 86% with IS5a and IS10a derived from tabaccoes, respectively.

On the other hand, they only had a homology of about 20 to 25% with the gene of an enzyme (Tanaka et al. (1996) Plant Cell and Physiology 37: 711–716; Frutek D, Schiefelbein JW, Johnston F, Nelson Jr. OE (1988) Plant Molecular Biology 11: 473–481, Wise RP, Rohde W, Salamini F. (1990) Plant Molecular Biology 14: 277–279) that glycosilates the position 3 of flavonoids and the gene of an enzyme (WO 99/05287) that glycosilates the position 5 of flavonoids, and therefore, it was estimated that both of Ph7GTa and Ph7GTb are the genes of flavonoid-7-glycosyl transferase as are pS.b UFGT1 and AmGT1.

Example 8

Expression of Ph7GTa and Ph7TGTb cDNA in *E. coli*

The Ph7GTa gene was expressed using the pET System (Stratagene). First, in order to introduce NdeI and BamHI sites, the following 2 primers pETPh7GTa5' [5'-ATA ACT ACA TAT GGC TAT TCC CAC A-3' (SEQ ID NO: 11)] and pETPh7GTa3' [5'-GAA CAG GAT CCT AAA AGG ACC T-3' (SEQ ID NO: 12)] were used in a PCR reaction.

The PCR reaction mixture was prepared in a total volume of 100 µl comprising 100 ng of pAmGT1, the 1×the cloned Pfu DNA polymerase reaction buffer (Stratagene), 0.2 mM dNTPs, 0.5 pmol/µl each of the primers, and 5.0 Units of the cloned Pfu DNA polymerase. The reaction was carried out, after 45 seconds at 95° C., for 25 cycles with one cycle comprising 95° C. for 45 seconds, 50° C. for 45 seconds, and 72° C. for 2 minutes, and was finally treated at 72° C. for 10 minutes. The PCR product obtained was subcloned into the pCR2.1 TOPO vector (INVITROGEN). Some of the clones of the plasmid pTOPO-ETPh7GTa thus obtained were reacted using ABI PRISM™ BigDye™ Terminator Cycle Sequencing Ready Reaction Kit (Applied Biosystems), and the entire nucleotide sequences were confirmed using DNA Sequencer model 310 (Applied Biosystems). An about 1.7 Kb fragment obtained by digesting pTOPO-ETPh7GTa with NdeI and BamHI was ligated to the NdeI and BamHI sites of the pET-3a vector (Stratagene) to obtain plasmid pETPh-GTa.

Using pETPhGTa, it was transformed into Epicurian Coli BL21 (DE3) (Stratagene).

For Ph7GTb also, in order to introduce NdeI and BamHI sites, the following 2 primers pETPh7GTb5'[5'-ATA ACT ACA TAT GGG TCA GCT CCA-3'(SEQ ID NO: 13)] and pETPh7GTb3'[5'-CTC GTA CCA TGG AAA ACT ATT CT-3' (SEQ ID NO: 14)] were used in a PCR reaction and then plasmid pETPhGTb was obtained.

Example 9

Measurement of the Glycosyl Transferase Activity of Ph7GTa. Ph7GTb cDNA Recombinant Proteins The transformants obtained in Example 8 were cultured, extracted and the enzymatic activity was measured as in Example 1. The enzymatic activity was measured using aureusidin as the substrate. The enzymatic activity was measured as described in Example 1. For Ph7GTa and Ph7GTb, a peak was obtained that had the same retention time and the same spectrum as aureusidin 6-glycoside as a reaction product. For Ph7GTa also, one peak, that is estimated to be an aurone glycoside from the absorption spectrum, was obtained, and for Ph7GTb two such peaks were obtained.

The foregoing results revealed that Ph7GTa and Ph7GTb encode enzymes having an activity of glycosilating aureusidin.

Industrial Applicability

Using the gene expression products obtained in the present invention, it was possible to glycosilate aurones. This enabled a stable expression of aurones in plant cells.

What is claimed is:

1. A gene encoding a protein that has an amino acid sequence as set forth in SEQ ID NO: 2, and that has an activity of transferring a glycosyl group to aurones.

2. A vector comprising a gene according to claim 1.

3. A host cell transformed with a vector according to claim 2.

4. A nucleotide sequence encoding a protein that has an amino acid sequence as set forth in SEQ ID NO: 2.

5. A vector into which the nucleotide sequence of claim 4 has been introduced.

6. A host cell transformed with a vector according to claim 5.

* * * * *

SEQUENCE LISTING

<160> NUMBER OF SEQ ID NOS: 14

<210> SEQ ID NO 1
<211> LENGTH: 1751
<212> TYPE: DNA
<213> ORGANISM: Antirrhinum majus
<220> FEATURE:
<221> NAME/KEY: misc_feature
<222> LOCATION: (1)..(1751)
<223> OTHER INFORMATION: Nucleotide sequence coding for a protein having glycosyl transferase to aurone
<221> NAME/KEY: CDS
<222> LOCATION: (76)..(1518)

<400> SEQUENCE: 1

```
ctcacttagt actaaaacac aaaactgaga acccttcaaa tttccacttg atcatattca         60
attttccttt taaaa atg gga aaa ctt cac att gcc tta ttt cca gtt atg        111
              Met Gly Lys Leu His Ile Ala Leu Phe Pro Val Met
                1               5                  10 gct cat ggt cac atg atc cca atg ttg gac atg gcc aag ctc ttt acc        159
Ala His Gly His Met Ile Pro Met Leu Asp Met Ala Lys Leu Phe Thr
         15                  20                  25 tca aga ggc ata caa aca aca atc att tcg act ctc gcc ttc gct gat        207
Ser Arg Gly Ile Gln Thr Thr Ile Ile Ser Thr Leu Ala Phe Ala Asp
 30                  35                  40 ccg ata aac aaa gct cgt gat tcg ggc ctc gat att gga cta agc atc        255
Pro Ile Asn Lys Ala Arg Asp Ser Gly Leu Asp Ile Gly Leu Ser Ile
 45                  50                  55                  60 ctc aaa ttc cca cca gaa gga tca gga ata cca gat cac atg gtg agc        303
Leu Lys Phe Pro Pro Glu Gly Ser Gly Ile Pro Asp His Met Val Ser
                 65                  70                  75 ctt gat cta gtt act gaa gat tgg ctc cca aag ttt gtt gag tca tta        351
Leu Asp Leu Val Thr Glu Asp Trp Leu Pro Lys Phe Val Glu Ser Leu
             80                  85                  90 gtc tta tta caa gag cca gtt gag aag ctt atc gaa gaa cta aag ctc        399
Val Leu Leu Gln Glu Pro Val Glu Lys Leu Ile Glu Glu Leu Lys Leu
         95                 100                 105 gac tgt ctc gtt tcc gac atg ttc ttg cct tgg aca gtc gat tgt gcg        447
Asp Cys Leu Val Ser Asp Met Phe Leu Pro Trp Thr Val Asp Cys Ala
110                 115                 120 gct aag ttc ggt att ccg agg ttg gtt ttc cac gga acg agc aac ttt        495
Ala Lys Phe Gly Ile Pro Arg Leu Val Phe His Gly Thr Ser Asn Phe
125                 130                 135                 140 gcg ttg tgt gct tcg gag caa atg aag ctt cac aag cct tat aag aat        543
Ala Leu Cys Ala Ser Glu Gln Met Lys Leu His Lys Pro Tyr Lys Asn
                145                 150                 155 gta act tct gat act gag aca ttt gtt ata ccg gat ttc ccg cat gag        591
Val Thr Ser Asp Thr Glu Thr Phe Val Ile Pro Asp Phe Pro His Glu
                160                 165                 170 ctg aag ttt gtg agg act caa gtg gct ccg ttt cag ctt gcg gaa acg        639
Leu Lys Phe Val Arg Thr Gln Val Ala Pro Phe Gln Leu Ala Glu Thr
            175                 180                 185
```

```
                                                                -continued gag aat gga ttc tca aag ttg atg aaa cag atg acg gag tct gtt ggt      687
Glu Asn Gly Phe Ser Lys Leu Met Lys Gln Met Thr Glu Ser Val Gly
    190                 195                 200 aga agc tac ggt gtt gtg gtt aac agt ttt tat gag ctc gag tcg act      735
Arg Ser Tyr Gly Val Val Val Asn Ser Phe Tyr Glu Leu Glu Ser Thr
205                 210                 215                 220 tat gtg gat tat tac aga gag gtt ttg ggt aga aag tct tgg aat ata      783
Tyr Val Asp Tyr Tyr Arg Glu Val Leu Gly Arg Lys Ser Trp Asn Ile
                225                 230                 235 ggg cct ctg ttg tta tcc aac aat ggc aat gag gaa aaa gta caa agg      831
Gly Pro Leu Leu Leu Ser Asn Asn Gly Asn Glu Glu Lys Val Gln Arg
            240                 245                 250 gga aag gaa tct gcg att ggc gaa cac gaa tgc ttg gct tgg ttg aat      879
Gly Lys Glu Ser Ala Ile Gly Glu His Glu Cys Leu Ala Trp Leu Asn
        255                 260                 265 tcc aag aag cag aat tcg gtt gtt tac gtt tgt ttt gga agt atg gcg      927
Ser Lys Lys Gln Asn Ser Val Val Tyr Val Cys Phe Gly Ser Met Ala
    270                 275                 280 act ttt act cca gcg cag ttg cgc gaa act gcg att gga ctc gag gaa      975
Thr Phe Thr Pro Ala Gln Leu Arg Glu Thr Ala Ile Gly Leu Glu Glu
285                 290                 295                 300 tca ggc caa gag ttc att tgg gta gtt aaa aag gcc aaa aac gaa gaa     1023
Ser Gly Gln Glu Phe Ile Trp Val Val Lys Lys Ala Lys Asn Glu Glu
                305                 310                 315 gaa gga aaa gga aaa gaa gaa tgg ctg cca gaa aat ttt gag gaa aga     1071
Glu Gly Lys Gly Lys Glu Glu Trp Leu Pro Glu Asn Phe Glu Glu Arg
            320                 325                 330 gtg aaa gat aga ggc ttg atc ata aga gga tgg gcg ccg caa ttg ttg     1119
Val Lys Asp Arg Gly Leu Ile Ile Arg Gly Trp Ala Pro Gln Leu Leu
        335                 340                 345 ata ctc gat cat cct gcg gta gga gct ttc gtg acg cat tgt gga tgg     1167
Ile Leu Asp His Pro Ala Val Gly Ala Phe Val Thr His Cys Gly Trp
    350                 355                 360 aat tcg acg ttg gaa gga ata tgc gcc ggt gtg cct atg gtg act tgg     1215
Asn Ser Thr Leu Glu Gly Ile Cys Ala Gly Val Pro Met Val Thr Trp
365                 370                 375                 380 cca gtt ttc gca gag cag ttt ttc aat gag aag ttt gtg aca gag gtt     1263
Pro Val Phe Ala Glu Gln Phe Phe Asn Glu Lys Phe Val Thr Glu Val
                385                 390                 395 ttg ggg acc ggt gtt tcg gtt ggg aat aag aag tgg cta agg gca gca     1311
Leu Gly Thr Gly Val Ser Val Gly Asn Lys Lys Trp Leu Arg Ala Ala
            400                 405                 410 agt gaa ggt gtg tcg agg gag gca gtg acg aac gcg gtg cag cgt gtt     1359
Ser Glu Gly Val Ser Arg Glu Ala Val Thr Asn Ala Val Gln Arg Val
        415                 420                 425 atg gtg gga gaa aat gcg tcg gag atg aga aag cga gcg aag tat tat     1407
Met Val Gly Glu Asn Ala Ser Glu Met Arg Lys Arg Ala Lys Tyr Tyr
    430                 435                 440 aag gaa atg gcg agg cgg gcg gtt gag gaa ggc ggt tcg tct tat aat     1455
Lys Glu Met Ala Arg Arg Ala Val Glu Glu Gly Gly Ser Ser Tyr Asn
445                 450                 455                 460 ggt ttg aat gag atg ata gag gat ttg agt gtg tac cgt gct cca gaa     1503
Gly Leu Asn Glu Met Ile Glu Asp Leu Ser Val Tyr Arg Ala Pro Glu
                465                 470                 475 aaa caa gac tta aac tagattctta tagatgactt ctagtgtgac aattgtaatt     1558
Lys Gln Asp Leu Asn
            480 ttttgccttt tattcaagtt tcctcattag tgttgagagc tttccctgta ttttcagaat   1618 tggtttgttc aatttttaca tgatttgtga tagatagctg catagtttct agctgttaac   1678
```

-continued

```
attgtttgat catattgagt tgatttaaaa tgagagtagc atgtgatctt cagattaaaa    1738
aaaaaaaaaa aaa                                                       1751

<210> SEQ ID NO 2
<211> LENGTH: 481
<212> TYPE: PRT
<213> ORGANISM: Antirrhinum majus
<220> FEATURE:
<223> OTHER INFORMATION: Amino acid sequence of a protein having
      glycosyl transferase to aurone

<400> SEQUENCE: 2

Met Gly Lys Leu His Ile Ala Leu Phe Pro Val Met Ala His Gly His
1               5                   10                  15

Met Ile Pro Met Leu Asp Met Ala Lys Leu Phe Thr Ser Arg Gly Ile
                20                  25                  30

Gln Thr Thr Ile Ile Ser Thr Leu Ala Phe Ala Asp Pro Ile Asn Lys
            35                  40                  45

Ala Arg Asp Ser Gly Leu Asp Ile Gly Leu Ser Ile Leu Lys Phe Pro
        50                  55                  60

Pro Glu Gly Ser Gly Ile Pro Asp His Met Val Ser Leu Asp Leu Val
65                  70                  75                  80

Thr Glu Asp Trp Leu Pro Lys Phe Val Glu Ser Leu Val Leu Leu Gln
                85                  90                  95

Glu Pro Val Glu Lys Leu Ile Glu Glu Leu Lys Leu Asp Cys Leu Val
                100                 105                 110

Ser Asp Met Phe Leu Pro Trp Thr Val Asp Cys Ala Ala Lys Phe Gly
            115                 120                 125

Ile Pro Arg Leu Val Phe His Gly Thr Ser Asn Phe Ala Leu Cys Ala
        130                 135                 140

Ser Glu Gln Met Lys Leu His Lys Pro Tyr Lys Asn Val Thr Ser Asp
145                 150                 155                 160

Thr Glu Thr Phe Val Ile Pro Asp Phe Pro His Glu Leu Lys Phe Val
                165                 170                 175

Arg Thr Gln Val Ala Pro Phe Gln Leu Ala Glu Thr Glu Asn Gly Phe
                180                 185                 190

Ser Lys Leu Met Lys Gln Met Thr Glu Ser Val Gly Arg Ser Tyr Gly
            195                 200                 205

Val Val Val Asn Ser Phe Tyr Glu Leu Glu Ser Thr Tyr Val Asp Tyr
        210                 215                 220

Tyr Arg Glu Val Leu Gly Arg Lys Ser Trp Asn Ile Gly Pro Leu Leu
225                 230                 235                 240

Leu Ser Asn Asn Gly Asn Glu Glu Lys Val Gln Arg Gly Lys Glu Ser
                245                 250                 255

Ala Ile Gly Glu His Glu Cys Leu Ala Trp Leu Asn Ser Lys Lys Gln
            260                 265                 270

Asn Ser Val Val Tyr Val Cys Phe Gly Ser Met Ala Thr Phe Thr Pro
        275                 280                 285

Ala Gln Leu Arg Glu Thr Ala Ile Gly Leu Glu Glu Ser Gly Gln Glu
    290                 295                 300

Phe Ile Trp Val Val Lys Lys Ala Lys Asn Glu Glu Gly Lys Gly
305                 310                 315                 320

Lys Glu Glu Trp Leu Pro Glu Asn Phe Glu Glu Arg Val Lys Asp Arg
                325                 330                 335
```

-continued

```
Gly Leu Ile Ile Arg Gly Trp Ala Pro Gln Leu Leu Ile Leu Asp His
            340                 345                 350
Pro Ala Val Gly Ala Phe Val Thr His Cys Gly Trp Asn Ser Thr Leu
        355                 360                 365
Glu Gly Ile Cys Ala Gly Val Pro Met Val Thr Trp Pro Val Phe Ala
370                 375                 380
Glu Gln Phe Phe Asn Glu Lys Phe Val Thr Glu Val Leu Gly Thr Gly
385                 390                 395                 400
Val Ser Val Gly Asn Lys Lys Trp Leu Arg Ala Ala Ser Glu Gly Val
                405                 410                 415
Ser Arg Glu Ala Val Thr Asn Ala Val Gln Arg Val Met Val Gly Glu
            420                 425                 430
Asn Ala Ser Glu Met Arg Lys Arg Ala Lys Tyr Tyr Lys Glu Met Ala
        435                 440                 445
Arg Arg Ala Val Glu Glu Gly Gly Ser Ser Tyr Asn Gly Leu Asn Glu
450                 455                 460
Met Ile Glu Asp Leu Ser Val Tyr Arg Ala Pro Glu Lys Gln Asp Leu
465                 470                 475                 480
Asn
```

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
ataactacat atgggacaac tccac                                    25

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
cagaacagga tccacacgta attta                                    25

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
ataactacat atgggaaaac ttcac                                    25

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
gaacaggatc cacacactag aagtca                                   26

<210> SEQ ID NO 7

```
<211> LENGTH: 1750
<212> TYPE: DNA
<213> ORGANISM: Petunia hybrida
<220> FEATURE:
<221> NAME/KEY: misc_feature
<222> LOCATION: (1)..(1750)
<223> OTHER INFORMATION: Nucleotide sequence coding for a protein having
      glycosyl transferase to aurone
<221> NAME/KEY: CDS
<222> LOCATION: (36)..(1499)

<400> SEQUENCE: 7
ccaaattctc tgatctttcc actaataatt tccca atg gct att ccc aca gtg                53
                                       Met Ala Ile Pro Thr Val
                                       1               5 caa cca cat ttt gtg ctg ctt cct ttc atg gca caa ggc cat aca aat              101
Gln Pro His Phe Val Leu Leu Pro Phe Met Ala Gln Gly His Thr Asn
            10                  15                  20 ccc atg att gac atc gca cgc cta ttg gca caa cgc gga gtt ata atc              149
Pro Met Ile Asp Ile Ala Arg Leu Leu Ala Gln Arg Gly Val Ile Ile
        25                  30                  35 acc att ctt act aca cac ttt aat gcc act aga ttc aag aca gtc gtt              197
Thr Ile Leu Thr Thr His Phe Asn Ala Thr Arg Phe Lys Thr Val Val
40                  45                  50 gat cgg gca gta gtg gca gca cta aag att cag gta gtt cac ctc tat              245
Asp Arg Ala Val Val Ala Ala Leu Lys Ile Gln Val Val His Leu Tyr
55                  60                  65                  70 ttt cca agc tta gag gct gga cta cct gaa ggg tgt gaa gct ttc gac              293
Phe Pro Ser Leu Glu Ala Gly Leu Pro Glu Gly Cys Glu Ala Phe Asp
                75                  80                  85 atg ctt cct tca atg gat ttc gca atg aaa ttc ttt gat gct acc agt              341
Met Leu Pro Ser Met Asp Phe Ala Met Lys Phe Phe Asp Ala Thr Ser
            90                  95                  100 agg ctt caa cca caa gtg gaa gaa atg ctt cat gaa ctg caa ccg tca              389
Arg Leu Gln Pro Gln Val Glu Glu Met Leu His Glu Leu Gln Pro Ser
        105                 110                 115 cca agt tgc ata ata tct gat atg tgt ttt cca tgg aca act aat gtt              437
Pro Ser Cys Ile Ile Ser Asp Met Cys Phe Pro Trp Thr Thr Asn Val
120                 125                 130 gca caa aaa ttc aac att cct agg ctt gtt ttt cat ggg atg tgc tgt              485
Ala Gln Lys Phe Asn Ile Pro Arg Leu Val Phe His Gly Met Cys Cys
135                 140                 145                 150 ttt tct tta ttg tgc ttg cac aat ttg aga gat tgg aag gag ttg gag              533
Phe Ser Leu Leu Cys Leu His Asn Leu Arg Asp Trp Lys Glu Leu Glu
                155                 160                 165 tct gat ata gaa tat ttt caa gtt cca gga tta cat gac aaa att gaa              581
Ser Asp Ile Glu Tyr Phe Gln Val Pro Gly Leu His Asp Lys Ile Glu
            170                 175                 180 tta aac aaa gct cag ctt tca aat att gtt aag cca aga ggt cct gat              629
Leu Asn Lys Ala Gln Leu Ser Asn Ile Val Lys Pro Arg Gly Pro Asp
        185                 190                 195 tgg aat gaa ttt gca gat caa ctg aag aaa gca gaa gaa gaa gct tat              677
Trp Asn Glu Phe Ala Asp Gln Leu Lys Lys Ala Glu Glu Glu Ala Tyr
200                 205                 210 ggg ata gta gct aat agc ttt gaa gag tta gaa cca gaa tat gtc aag              725
Gly Ile Val Ala Asn Ser Phe Glu Glu Leu Glu Pro Glu Tyr Val Lys
215                 220                 225                 230 gga ttg gaa aag gca aaa ggc ttg aaa att tgg cca att ggt cct gtt              773
Gly Leu Glu Lys Ala Lys Gly Leu Lys Ile Trp Pro Ile Gly Pro Val
                235                 240                 245 tct ttg tgc aac aaa gag aaa cag gac aag gct gaa aga gga aac aag              821
Ser Leu Cys Asn Lys Glu Lys Gln Asp Lys Ala Glu Arg Gly Asn Lys
```

-continued

```
gct tca att gat gaa cac cag tgt cta aaa tgg cta gat tct tgg gga      869
Ala Ser Ile Asp Glu His Gln Cys Leu Lys Trp Leu Asp Ser Trp Gly
        265                 270                 275 gca aac tct gta ctc ttt gta tgt ctc ggg agc cta tcg cgc ctt cca      917
Ala Asn Ser Val Leu Phe Val Cys Leu Gly Ser Leu Ser Arg Leu Pro
    280                 285                 290 acg cca caa atg ata gag ctg gga ctt ggc tta gaa tcg tcg aaa aga      965
Thr Pro Gln Met Ile Glu Leu Gly Leu Gly Leu Glu Ser Ser Lys Arg
295                 300                 305                 310 ccc ttt att tgg gtt gtt aga cac aag tca gat gaa ttt aaa agt tgg     1013
Pro Phe Ile Trp Val Val Arg His Lys Ser Asp Glu Phe Lys Ser Trp
                315                 320                 325 cta gtt gaa gaa aat ttt gag gaa aga gtt aaa gga caa gga ctt tta     1061
Leu Val Glu Glu Asn Phe Glu Glu Arg Val Lys Gly Gln Gly Leu Leu
            330                 335                 340 atc cat ggt tgg gca cca caa gta cta ata tta tct cac act tca att     1109
Ile His Gly Trp Ala Pro Gln Val Leu Ile Leu Ser His Thr Ser Ile
        345                 350                 355 gga gga ttc ttg act cat tgt gga tgg aat tcg agt gtc gaa gga ata     1157
Gly Gly Phe Leu Thr His Cys Gly Trp Asn Ser Ser Val Glu Gly Ile
    360                 365                 370 tct gca ggc gtt cca atg atc act tgg cca atg ttt gct gaa caa ttc     1205
Ser Ala Gly Val Pro Met Ile Thr Trp Pro Met Phe Ala Glu Gln Phe
375                 380                 385                 390 tgt aat gaa agg cta ata gtg aat gta ctg aag aca gga gta aag gct     1253
Cys Asn Glu Arg Leu Ile Val Asn Val Leu Lys Thr Gly Val Lys Ala
                395                 400                 405 gga att gag aat cct gtt atg ttt gga gag gaa gaa aaa gtt gga gca     1301
Gly Ile Glu Asn Pro Val Met Phe Gly Glu Glu Glu Lys Val Gly Ala
            410                 415                 420 caa gtg agc aaa gat gat att aag atg gtt att gaa aga gtc atg ggc     1349
Gln Val Ser Lys Asp Asp Ile Lys Met Val Ile Glu Arg Val Met Gly
        425                 430                 435 gaa gaa gag gaa gct gaa atg aga aga aaa aga gca aaa gag tta gga     1397
Glu Glu Glu Glu Ala Glu Met Arg Arg Lys Arg Ala Lys Glu Leu Gly
    440                 445                 450 gaa aag gca aag agg gct atg gag gaa ggg ggt tcc tca cac ttc aac     1445
Glu Lys Ala Lys Arg Ala Met Glu Glu Gly Gly Ser Ser His Phe Asn
455                 460                 465                 470 ttg aca cag ttg att caa gat gtc act gag caa gca aat att tta aaa     1493
Leu Thr Gln Leu Ile Gln Asp Val Thr Glu Gln Ala Asn Ile Leu Lys
                475                 480                 485 tcc atc taggattata aagtcgattc caagttcctt ttacgatcaa tttctaacca     1549
Ser Ile tctactagag atggtaacaa tccaaactgc gccttttttg cacaataatt attgttttat     1609
gttcagctag cacaaaaagt ttactattag tagaaatatt tcagctggaa ctgccgaact     1669
gctatgtaca ctgatggaac aatgtatgtc atgctattca aattaactct gagctgaaaa     1729
tatcatatag gagctgattt t                                              1750
```

<210> SEQ ID NO 8
<211> LENGTH: 488
<212> TYPE: PRT
<213> ORGANISM: Petunia hybrida
<220> FEATURE:
<223> OTHER INFORMATION: Amino acid sequence of a protein having
      glycosyl transferase to aurone

<400> SEQUENCE: 8

```
Met Ala Ile Pro Thr Val Gln Pro His Phe Val Leu Pro Phe Met
1               5                   10                  15

Ala Gln Gly His Thr Asn Pro Met Ile Asp Ile Ala Arg Leu Leu Ala
                20                  25                  30

Gln Arg Gly Val Ile Ile Thr Ile Leu Thr Thr His Phe Asn Ala Thr
            35                  40                  45

Arg Phe Lys Thr Val Val Asp Arg Ala Val Ala Ala Leu Lys Ile
        50                  55                  60

Gln Val His Leu Tyr Phe Pro Ser Leu Glu Ala Gly Leu Pro Glu
65              70                  75                  80

Gly Cys Glu Ala Phe Asp Met Leu Pro Ser Met Asp Phe Ala Met Lys
                85                  90                  95

Phe Phe Asp Ala Thr Ser Arg Leu Gln Pro Gln Val Glu Glu Met Leu
                100                 105                 110

His Glu Leu Gln Pro Ser Pro Ser Cys Ile Ile Ser Asp Met Cys Phe
            115                 120                 125

Pro Trp Thr Thr Asn Val Ala Gln Lys Phe Asn Ile Pro Arg Leu Val
        130                 135                 140

Phe His Gly Met Cys Cys Phe Ser Leu Leu Cys Leu His Asn Leu Arg
145                 150                 155                 160

Asp Trp Lys Glu Leu Glu Ser Asp Ile Glu Tyr Phe Gln Val Pro Gly
                165                 170                 175

Leu His Asp Lys Ile Glu Leu Asn Lys Ala Gln Leu Ser Asn Ile Val
            180                 185                 190

Lys Pro Arg Gly Pro Asp Trp Asn Glu Phe Ala Asp Gln Leu Lys Lys
        195                 200                 205

Ala Glu Glu Ala Tyr Gly Ile Val Ala Asn Ser Phe Glu Glu Leu
210                 215                 220

Glu Pro Glu Tyr Val Lys Gly Leu Glu Lys Ala Lys Gly Leu Lys Ile
225                 230                 235                 240

Trp Pro Ile Gly Pro Val Ser Leu Cys Asn Lys Glu Lys Gln Asp Lys
            245                 250                 255

Ala Glu Arg Gly Asn Lys Ala Ser Ile Asp Glu His Gln Cys Leu Lys
                260                 265                 270

Trp Leu Asp Ser Trp Gly Ala Asn Ser Val Leu Phe Val Cys Leu Gly
        275                 280                 285

Ser Leu Ser Arg Leu Pro Thr Pro Gln Met Ile Glu Leu Gly Leu Gly
    290                 295                 300

Leu Glu Ser Ser Lys Arg Pro Phe Ile Trp Val Val Arg His Lys Ser
305                 310                 315                 320

Asp Glu Phe Lys Ser Trp Leu Val Glu Glu Asn Phe Glu Glu Arg Val
                325                 330                 335

Lys Gly Gln Gly Leu Leu Ile His Gly Trp Ala Pro Gln Val Leu Ile
            340                 345                 350

Leu Ser His Thr Ser Ile Gly Gly Phe Leu Thr His Cys Gly Trp Asn
        355                 360                 365

Ser Ser Val Glu Gly Ile Ser Ala Gly Val Pro Met Ile Thr Trp Pro
    370                 375                 380

Met Phe Ala Glu Gln Phe Cys Asn Glu Arg Leu Ile Val Asn Val Leu
385                 390                 395                 400

Lys Thr Gly Val Lys Ala Gly Ile Glu Asn Pro Val Met Phe Gly Glu
            405                 410                 415
```

```
Glu Glu Lys Val Gly Ala Gln Val Ser Lys Asp Asp Ile Lys Met Val
            420                 425                 430

Ile Glu Arg Val Met Gly Glu Glu Glu Ala Glu Met Arg Arg Lys
        435                 440                 445

Arg Ala Lys Glu Leu Gly Lys Ala Lys Arg Ala Met Glu Glu Gly
    450                 455                 460

Gly Ser Ser His Phe Asn Leu Thr Gln Leu Ile Gln Asp Val Thr Glu
465             470                 475                 480

Gln Ala Asn Ile Leu Lys Ser Ile
                485

<210> SEQ ID NO 9
<211> LENGTH: 1669
<212> TYPE: DNA
<213> ORGANISM: Petunia hybrida
<220> FEATURE:
<221> NAME/KEY: misc_feature
<222> LOCATION: (1)..(1669)
<223> OTHER INFORMATION: Nucleotide sequence coding for a protein having
      glycosyl transferase to aurone
<221> NAME/KEY: CDS
<222> LOCATION: (114)..(1541)

<400> SEQUENCE: 9
```

| | | |
|---|---|---|
| atctctctct ctctctcctg aaaagaaacc cacaacggtt ttacttatcc ttttgttttc | 60 | |
| tgctaagtac tactactagt acacatcttt ctttctatca aacactttcc aaa atg<br>                                                                      Met<br>       1 | 116 | |

```
ggt cag ctc cat ttt ttc ttc ttt ccc atg atg gct cat ggc cac atg      164
Gly Gln Leu His Phe Phe Phe Phe Pro Met Met Ala His Gly His Met
        5                   10                  15 att cct aca cta gac atg gct aag ctt ttc gct tca cgt ggt gtt aag      212
Ile Pro Thr Leu Asp Met Ala Lys Leu Phe Ala Ser Arg Gly Val Lys
            20                  25                  30 gcc acc ata atc act act cct ctc aat gaa tca gtt ttc tcc aaa gct      260
Ala Thr Ile Ile Thr Thr Pro Leu Asn Glu Ser Val Phe Ser Lys Ala
 35                  40                  45 att gaa aga aac aag cat gaa att gac atc cgt ttg atc aaa ttc caa      308
Ile Glu Arg Asn Lys His Glu Ile Asp Ile Arg Leu Ile Lys Phe Gln
 50                  55                  60                  65 gct gtt gaa aat ggc ttg cct gaa ggt tgt gag cgt att gat ctt atc      356
Ala Val Glu Asn Gly Leu Pro Glu Gly Cys Glu Arg Ile Asp Leu Ile
                 70                  75                  80 cct tct gat gac aag ctt tcc aat ttt ttg aaa gct gca gct atg atg      404
Pro Ser Asp Asp Lys Leu Ser Asn Phe Leu Lys Ala Ala Ala Met Met
             85                  90                  95 caa gaa cca ctt gag cag ctt att gaa gaa tgt cat ccc aat tgt ctt      452
Gln Glu Pro Leu Glu Gln Leu Ile Glu Glu Cys His Pro Asn Cys Leu
        100                 105                 110 gtt tct gat atg ttc ctt cct tgg act act gat act gca gcc aag ttt      500
Val Ser Asp Met Phe Leu Pro Trp Thr Thr Asp Thr Ala Ala Lys Phe
    115                 120                 125 aac att cca aga ata gtt ttc cat ggt acg agt ttc ttt gca ctt tgt      548
Asn Ile Pro Arg Ile Val Phe His Gly Thr Ser Phe Phe Ala Leu Cys
130                 135                 140                 145 gta gag aat agt aac agg act aat aag cca ttc aag aac gtc tct tct      596
Val Glu Asn Ser Asn Arg Thr Asn Lys Pro Phe Lys Asn Val Ser Ser
                150                 155                 160 gat tct gaa act ttt gtt gta cca aat ttg cct cac gaa atc agg cta      644
Asp Ser Glu Thr Phe Val Val Pro Asn Leu Pro His Glu Ile Arg Leu
            165                 170                 175
```

-continued

```
act aga aca caa ttg tct ccg ttt gag caa tca ttg gaa gag aca cca      692
Thr Arg Thr Gln Leu Ser Pro Phe Glu Gln Ser Leu Glu Glu Thr Pro
        180                 185                 190 atg tcc cga atg ata aaa gca gtt agg gaa tcg gac gcg aag agt tat      740
Met Ser Arg Met Ile Lys Ala Val Arg Glu Ser Asp Ala Lys Ser Tyr
    195                 200                 205 gga gtt atc ttc aac agc ttc tat gag ctt gaa tca gat tat gtt gaa      788
Gly Val Ile Phe Asn Ser Phe Tyr Glu Leu Glu Ser Asp Tyr Val Glu
210                 215                 220                 225 cat tat acc aag gtt ctt ggt aga aag tct tgg gct att ggc ccg ctt      836
His Tyr Thr Lys Val Leu Gly Arg Lys Ser Trp Ala Ile Gly Pro Leu
                230                 235                 240 tct ttg tgc aat agg gac att gaa gat aaa gct gaa aga ggg aag att      884
Ser Leu Cys Asn Arg Asp Ile Glu Asp Lys Ala Glu Arg Gly Lys Ile
            245                 250                 255 tcc tct att gat aaa cat gag tgt ttg aat tgg ctt gat tca aag aaa      932
Ser Ser Ile Asp Lys His Glu Cys Leu Asn Trp Leu Asp Ser Lys Lys
        260                 265                 270 cca agt tcc att gtt tat gtt tgc ttc ggg agc gta gca gat ttc act      980
Pro Ser Ser Ile Val Tyr Val Cys Phe Gly Ser Val Ala Asp Phe Thr
    275                 280                 285 gca gca caa atg cgt gaa ctt gca ttg gga att gaa gca tct gga caa     1028
Ala Ala Gln Met Arg Glu Leu Ala Leu Gly Ile Glu Ala Ser Gly Gln
290                 295                 300                 305 gaa ttc att tgg gct gtt aga aga ggc aaa gag gaa caa gac aat gaa     1076
Glu Phe Ile Trp Ala Val Arg Arg Gly Lys Glu Glu Gln Asp Asn Glu
                310                 315                 320 gag tgg ttg cct gaa gga ttc gag gaa aga acg aaa gaa aaa ggt cta     1124
Glu Trp Leu Pro Glu Gly Phe Glu Glu Arg Thr Lys Glu Lys Gly Leu
            325                 330                 335 att att aga gga tgg gcg ccc caa gtg cta att ctt gat cac caa gct     1172
Ile Ile Arg Gly Trp Ala Pro Gln Val Leu Ile Leu Asp His Gln Ala
        340                 345                 350 gtg gga gct ttt gtc act cat tgt ggt tgg aat tca acg ctt gaa gga     1220
Val Gly Ala Phe Val Thr His Cys Gly Trp Asn Ser Thr Leu Glu Gly
    355                 360                 365 gta tca gca ggg gtg cct atg gtg acc tgg cct gtg ttt gca gag caa     1268
Val Ser Ala Gly Val Pro Met Val Thr Trp Pro Val Phe Ala Glu Gln
370                 375                 380                 385 ttt ttc aat gaa aag ttg gtg act gag gtt ttg aga act ggg gct ggt     1316
Phe Phe Asn Glu Lys Leu Val Thr Glu Val Leu Arg Thr Gly Ala Gly
                390                 395                 400 gtt ggt tca atg caa tgg aaa aga tca gct agc gag gga gta aaa agg     1364
Val Gly Ser Met Gln Trp Lys Arg Ser Ala Ser Glu Gly Val Lys Arg
            405                 410                 415 gaa gca ata gct aag gca ata aag aga gtc atg gtg agt gaa gaa gca     1412
Glu Ala Ile Ala Lys Ala Ile Lys Arg Val Met Val Ser Glu Glu Ala
        420                 425                 430 gag gga ttc aga aac cga gct aaa gcc tac aaa gag atg gca aaa caa     1460
Glu Gly Phe Arg Asn Arg Ala Lys Ala Tyr Lys Glu Met Ala Lys Gln
    435                 440                 445 gct att gaa gaa gga gga tct tct tac tct gga ttg act act ttg cta     1508
Ala Ile Glu Glu Gly Gly Ser Ser Tyr Ser Gly Leu Thr Thr Leu Leu
450                 455                 460                 465 caa gat ata agt aca tat agt tcc aaa agt cat taactgcaca actaaaaaaa  1561
Gln Asp Ile Ser Thr Tyr Ser Ser Lys Ser His
                470                 475 tgtagtgttg ttctatacaa tttttatgct tttttatgcg tgtactaatt taaacatgga  1621
```
tttagtgaca gcactttttg ttacttctta taatgacatt tcggatgg        1669

<210> SEQ ID NO 10
<211> LENGTH: 476
<212> TYPE: PRT
<213> ORGANISM: Petunia hybrida
<220> FEATURE:
<223> OTHER INFORMATION: Amino acid sequence coding of a protein having
      glycosyl transferase to aurone

<400> SEQUENCE: 10

```
Met Gly Gln Leu His Phe Phe Phe Pro Met Met Ala His Gly His
1               5                   10                  15

Met Ile Pro Thr Leu Asp Met Ala Lys Leu Phe Ala Ser Arg Gly Val
                20                  25                  30

Lys Ala Thr Ile Ile Thr Thr Pro Leu Asn Glu Ser Val Phe Ser Lys
                35                  40                  45

Ala Ile Glu Arg Asn Lys His Glu Ile Asp Ile Arg Leu Ile Lys Phe
        50                  55                  60

Gln Ala Val Glu Asn Gly Leu Pro Gly Cys Glu Arg Ile Asp Leu
65                  70                  75                  80

Ile Pro Ser Asp Asp Lys Leu Ser Asn Phe Leu Lys Ala Ala Met
                85                  90                  95

Met Gln Glu Pro Leu Glu Gln Leu Ile Glu Glu Cys His Pro Asn Cys
                100                 105                 110

Leu Val Ser Asp Met Phe Leu Pro Trp Thr Thr Asp Thr Ala Ala Lys
        115                 120                 125

Phe Asn Ile Pro Arg Ile Val Phe His Gly Thr Ser Phe Phe Ala Leu
        130                 135                 140

Cys Val Glu Asn Ser Asn Arg Thr Asn Lys Pro Phe Lys Asn Val Ser
145                 150                 155                 160

Ser Asp Ser Glu Thr Phe Val Val Pro Asn Leu Pro His Glu Ile Arg
                165                 170                 175

Leu Thr Arg Thr Gln Leu Ser Pro Phe Glu Gln Ser Leu Glu Glu Thr
        180                 185                 190

Pro Met Ser Arg Met Ile Lys Ala Val Arg Glu Ser Asp Ala Lys Ser
        195                 200                 205

Tyr Gly Val Ile Phe Asn Ser Phe Tyr Glu Leu Glu Ser Asp Tyr Val
        210                 215                 220

Glu His Tyr Thr Lys Val Leu Gly Arg Lys Ser Trp Ala Ile Gly Pro
225                 230                 235                 240

Leu Ser Leu Cys Asn Arg Asp Ile Glu Asp Lys Ala Glu Arg Gly Lys
                245                 250                 255

Ile Ser Ser Ile Asp Lys His Glu Cys Leu Asn Trp Leu Asp Ser Lys
        260                 265                 270

Lys Pro Ser Ser Ile Val Tyr Val Cys Phe Gly Ser Val Ala Asp Phe
        275                 280                 285

Thr Ala Ala Gln Met Arg Glu Leu Ala Leu Gly Ile Glu Ala Ser Gly
        290                 295                 300

Gln Glu Phe Ile Trp Ala Val Arg Arg Gly Lys Glu Glu Gln Asp Asn
305                 310                 315                 320

Glu Glu Trp Leu Pro Glu Gly Phe Glu Glu Arg Thr Lys Glu Lys Gly
                325                 330                 335

Leu Ile Ile Arg Gly Trp Ala Pro Gln Val Leu Ile Leu Asp His Gln
        340                 345                 350
```

```
Ala Val Gly Ala Phe Val Thr His Cys Gly Trp Asn Ser Thr Leu Glu
        355                 360                 365

Gly Val Ser Ala Gly Val Pro Met Val Thr Trp Pro Val Phe Ala Glu
    370                 375                 380

Gln Phe Phe Asn Glu Lys Leu Val Thr Glu Val Leu Arg Thr Gly Ala
385                 390                 395                 400

Gly Val Gly Ser Met Gln Trp Lys Arg Ser Ala Ser Glu Gly Val Lys
                405                 410                 415

Arg Glu Ala Ile Ala Lys Ala Ile Lys Arg Val Met Val Ser Glu Glu
            420                 425                 430

Ala Glu Gly Phe Arg Asn Arg Ala Lys Ala Tyr Lys Glu Met Ala Lys
        435                 440                 445

Gln Ala Ile Glu Glu Gly Gly Ser Ser Tyr Ser Gly Leu Thr Thr Leu
    450                 455                 460

Leu Gln Asp Ile Ser Thr Tyr Ser Ser Lys Ser His
465                 470                 475

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
ataactacat atggctattc ccaca                                        25

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
gaacaggatc ctaaaaggac ct                                           22

<210> SEQ ID NO 13
<211> LENGTH: 24
<212> TYPE: DNA
<213> ORGANISM: Artificial Sequence
<220> FEATURE:
<223> OTHER INFORMATION: Primer

<400> SEQUENCE: 13
ataactacat atgggtcagc tcca                                         24

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
ctcgtaccat ggaaaactat tct                                          23
```